United States Patent [19]
Smith et al.

[11] Patent Number: 4,542,646
[45] Date of Patent: Sep. 24, 1985

[54] TABLET HARDNESS TESTER

[75] Inventors: Daniel J. Smith, Parchment; Jessie F. Glasscock, Jr.; Richard P. Poska, both of Kalamazoo; Carl L. Kuder, Brady Township, Kalamazoo County, all of Mich.

[73] Assignee: The Upjohn Company, Kalamazoo, Mich.

[21] Appl. No.: 659,993

[22] Filed: Oct. 12, 1984

[51] Int. Cl.⁴ ............................ G01N 3/40; G01N 3/08
[52] U.S. Cl. ............................................ 73/78; 73/821
[58] Field of Search ...................................... 73/78, 821

[56] References Cited

U.S. PATENT DOCUMENTS

| | | | |
|---|---|---|---|
| 2,975,630 | 3/1961 | Mitchel | 73/78 |
| 3,757,566 | 9/1973 | Flory . | |
| 3,943,759 | 3/1976 | Wilhelm | 73/78 |
| 4,022,056 | 5/1977 | Barland . | |
| 4,236,413 | 12/1980 | Schmid et al. | 73/821 |
| 4,393,717 | 7/1983 | Meyers . | |
| 4,472,960 | 9/1984 | Motoyama | 73/78 |

FOREIGN PATENT DOCUMENTS 3130512  8/1980  Fed. Rep. of Germany .

OTHER PUBLICATIONS

Copy of Brochure entitled "HT 300 Peluiag", one sheet 1980.
Copy of Brochure entitled "Key Tablet Hardness Tester", two sheets 1980.

Primary Examiner—S. Clement Swisher
Attorney, Agent, or Firm—Flynn, Thiel, Boutell & Tanis

[57] ABSTRACT

An improved tablet hardness tester includes a ram and anvil for fracturing a tablet therebetween, a support for holding a tablet in position for fracturing between the ram and anvil, a strain gauge for measuring the force exerted by the ram in fracturing the tablet, and an indicator for indicating the measured force. The support according to the invention is a plurality of spaced-apart elongated member, preferably a pair of parallel wires. A tablet is placed on these wires and then crushed by the ram and anvil so that the pieces of the broken tablet fall beneath the wires into a container, thus eliminating the need for cleaning the support prior to a subsequent tablet hardness measurement.

22 Claims, 8 Drawing Figures

TABLET HARDNESS TESTER

FIELD OF THE INVENTION

This invention relates to an improved tablet hardness tester for measuring the force required to fracture a pharmaceutical tablet, and particularly a hardness tester wherein the fracturing zone of the hardness tester is self-cleaning. According to this invention, a series of identical tablets can be automatically tested, and a digital readout of the measured hardness values obtained.

BACKGROUND OF THE INVENTION

In tablet formulation, it is important to accurately measure the hardness of a tablet containing a pharmaceutically active material, since the hardness of a tablet in part determines where the tablet will dissolve in the digestive tract. Tablet hardness is conventionally measured by determining the force required to fracture a tablet along its lengthwise axis. Numerous devices have been conventionally used to make such measurements. As general features, these prior art devices typically include a ram and anvil for crushing a tablet therebetween, and a strain gauge for measuring the amount of force required to fracture the tablet. U.S. Pat. Nos. 2,645,936, 2,041,869 and 2,975,630 disclose simple hand-operated hardness testers having these features.

More recent hardness testers include a frame so that the tester can be securely positioned on a work surface such as a table. U.S. Pat. No. 3,757,566 discloses a hardness tester wherein a tablet is placed in a groove defined between a pressure slide and a measuring slide. The tablet is crushed between these two slides, and the tablet powder must then be brushed away before another tablet can be tested. This prior art device has the disadvantage that tablet powder can work its way between the two slides, eventually fouling the mechanism.

U.S. Pat. No. 4,022,056 discloses a hardness tester wherein an anvil and hammer are disposed in a vertical relationship. This device has the disadvantages that the operator must again brush fragments and powder of the broken tablet off of the anvil, and delicately position the tablet on edge beneath the anvil.

U.S. Pat. No. 4,393,717 discloses an apparatus for measuring the thickness, diameter and hardness of medicinal tablets. According to this device, tablets to be tested are fed from a rotating carousel down an inclined trough onto a support. The tablet is then measured and crushed, and the broken tablet is removed by a scraper. This patent discloses a system which automatically tests a series of tablets, but the system disclosed by this patent is highly complicated, requiring a vibrator for causing a tablet to move down the trough, and a photosensing device for determining when a tablet has fallen from the end of the trough onto the support surface.

All of the foregoing prior art hardness testers share the problem that the fracturing zone of the tester must be cleaned before a new tablet can be tested. In the prior art, such cleaning is carried out by manual brushing of the apparatus, or by an automatic scraping device. None of the prior art hardness testers are self-cleaning in the sense that a separate operation for cleaning the fracturing zone is needed. Most conventional hardness testers are manually loaded, and incapable of carrying out a series of hardness measuring operations without human intervention.

It is an object of the present invention to provide a self-cleaning hardness tester which requires substantially no cleaning after a tablet has been fractured, by either a human operator or by an automatic device such as a scraper. It is a further object of the invention to provide an improved tablet dispenser for a hardness tester, which tablet dispenser is capable of reliably placing tablets one-by-one on a support surface for hardness testing, without need for complex structures such as a vibrating trough or photosensor. A further object of the invention is to provide a hardness tester which can be connected to a digital transducer indicator so that digital hardness readings can be obtained.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the device and designated parts thereof. This terminology will include the foregoing words, derivatives thereof, and words of similar meaning.

SUMMARY OF THE INVENTION

The present invention is an apparatus for measuring tablet hardness which includes a ram and anvil for crushing a tablet, a support on which the tablet rests so that it is in position to be crushed, and a gauge for measuring the minimum force exerted by the ram and anvil to fracture the tablet. The support comprises a plurality of spaced-apart, elongated support members which support the tablet on its underside. These support members have a diameter small enough so that pieces of the tablet fall downwardly below the support members after the tablet has been fractured. In a preferred embodiment, a pair of spaced-apart, parallel wires disposed just below the path of the ram and parallel to the direction of travel thereof are used as the support members.

The present invention further pertains to an improved hardness tester which includes a reciprocating, vertically movable tablet dispenser for placing tablets one at a time on the support members. The tablet dispenser has a central, vertically extending bore in which a vertical stack of tablets is held. The bore is open at the lower end thereof, and the stack is retained therein by a pair of retaining arms, which arms frictionally engage the edge of the lowermost tablet at opposite sides thereof, thereby holding the entire stack of tablets within the bore. To supply a new tablet for testing onto the support members, the tablet dispenser is lowered to a specific position at which the lowermost tablet in the stack is one tablet thickness above the support members. The retaining arms then release the lowermost tablet, and the entire stack of tablets moves downwardly in the bore by a distance equal to one tablet thickness. The retaining arms are then moved into engagement with the tablet adjacent the lowermost tablet in the stack, and the dispenser then moves upwardly, leaving the lowermost tablet on the support members and retaining the remainder of the stack within the bore. The tablet dispenser then continues to move upwardly out of the way of the ram, and then the tablet on the support members is crushed by the action of the ram and anvil, and its hardness is thereby measured.

DETAILED DESCRIPTION

Figure 1:
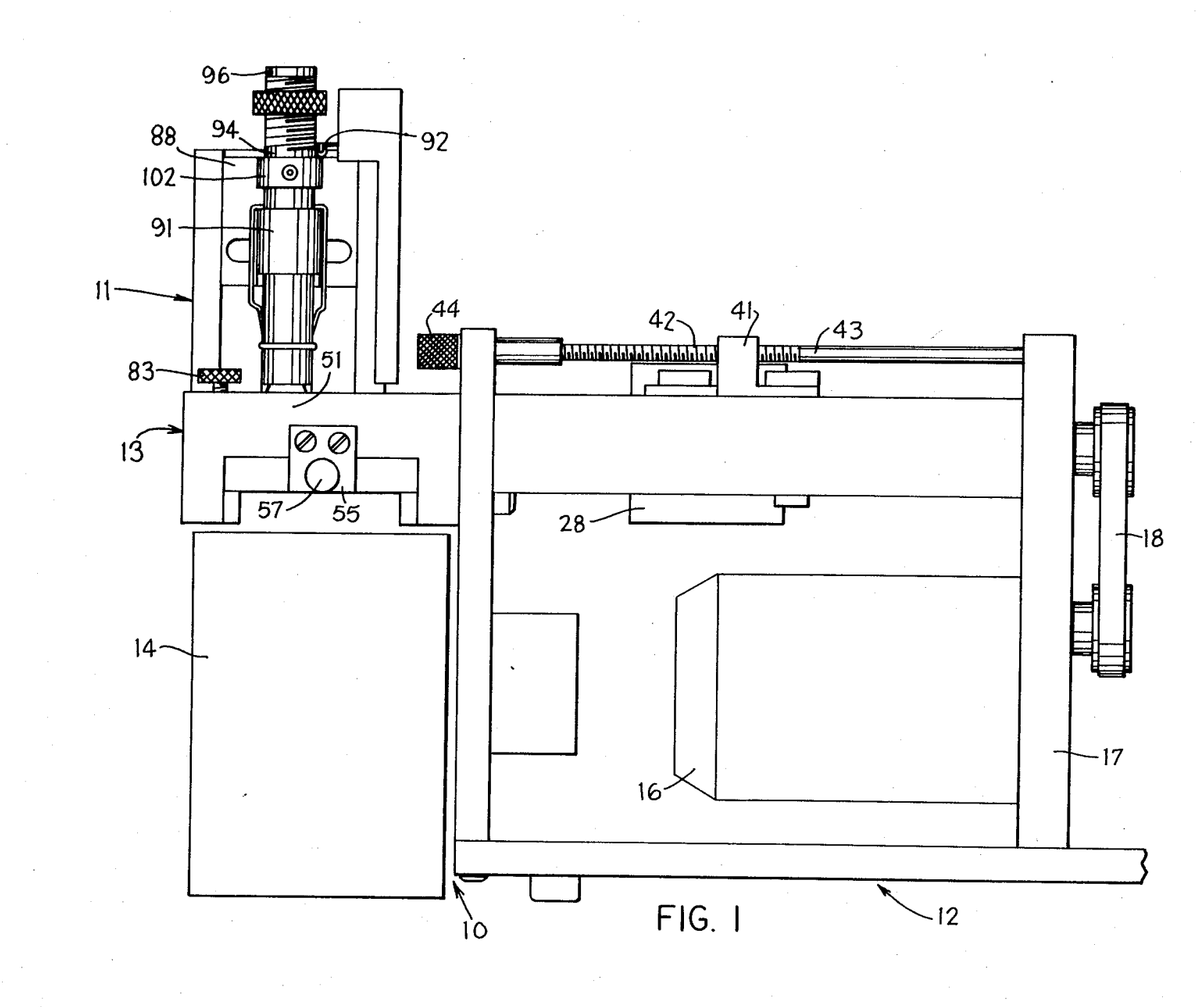
FIG. 1 is a front view of a hardness tester according to the present invention.

FIG. 1 illustrates a preferred embodiment of a hardness tester 10 according to the present invention. The hardness tester 10 includes a tablet dispensing mechanism 11, a ram mechanism 12 and a tablet support mechanism 13. The tablet support mechanism 13 is built onto the front of the ram mechanism 12, and the dispensing mechanism 11 is positioned above the tablet support mechanism 13. A receptacle or box 14 is disposed beneath the supporting mechanism 13 to catch pieces of broken tablets which are fractured by the ram mechanism 12.

The ram mechanism 12, as shown in FIG. 1, includes a motor 16 mounted on a rectangular housing or frame 17, which frame 17 is supported on a work surface such as a table-top. A belt-pulley drive train 18 transmits the rotation of motor 16 to a threaded drive shaft 26 (FIG. 2) which is rotatably supported on the frame. The drive shaft 26 activates the ram assembly 23, and for this purpose is threadedly coupled with a threaded bore (not shown) of a cylindrical sleeve 27. The front end of sleeve 27 is coupled to the rear end of a conventional strain gauge transducer 28, and the rear end of a cylindrical ram 29 is connected to the front end of transducer 28. In a preferred embodiment, an Ametek transducer serving a CA-100 load cell is connected to an Ametek peak hold digital transducer indicator Model HSC-11. A lateral bracket 31 is mounted on top of the sleeve 27 and transducer 28 for integral movement therewith. The ram 29 slidably extends through a close-fitting hole 30 in the front wall 22 of the frame 17. The ram assembly 23, which includes the sleeve 27, transducer 28 and ram 29, is connected to a pair of parallel linear bushings 32 and 33 by means of the bracket 31. The linear bushings 32, 33 are respectively mounted on stationary guide shafts 34, 35 mounted parallel to the direction of travel of the ram 29 and on opposite sides thereof.

Figure 2:
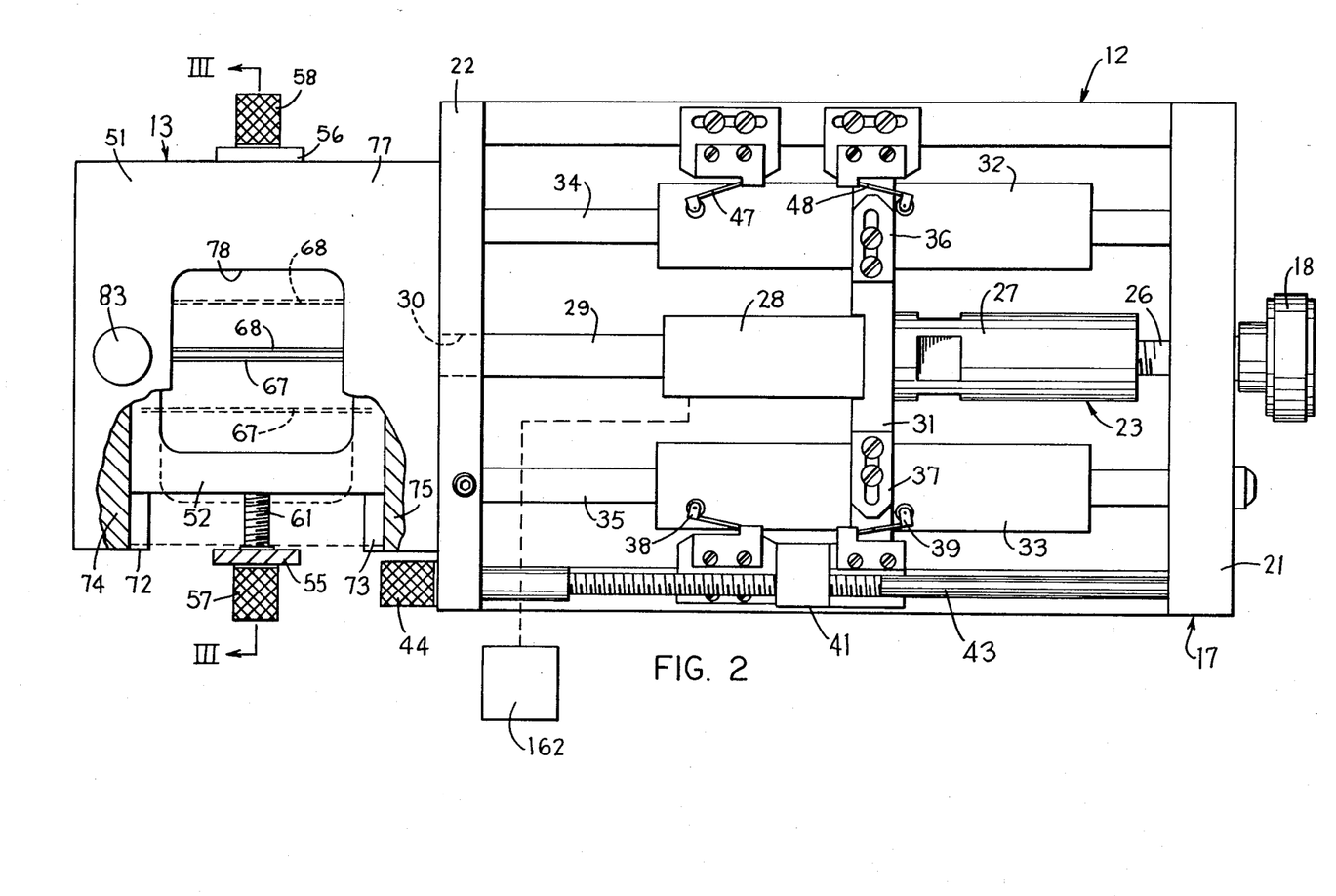
FIG. 2 is a top plan view, partly in section, of the hardness tester shown in FIG. 1, but with the tablet dispenser removed.

A threaded shaft 43 extends between and is rotatably mounted on the front wall 22 and rear wall 21 of the frame 17, which shaft 43 is also parallel to the ram assembly 23. A slidable mount 41 is threadedly coupled to the shaft 43. A rear limit switch 39 is fixedly mounted on the mount 41. The position of the rear limit switch 39 can be adjusted by turning a knob 44 and thereby rotating the threaded shaft 43 to cause linear displacement of mount 41. A front limit switch 38 is adjustably mounted on the frame 17 forwardly of the rear limit switch 39. A pair of front and rear safety limit switches 47 and 48 are mounted on the frame 17 on the opposite side of the ram assembly 23 from the limit switches 38 and 39. Both sets of limit switches are positioned to contact an associated edge of one of the split adjustable cams 36 or 37 as carried by the bracket 31. The limit switch 38 is tripped when the ram assembly 23 and linear bushings 32, 33 reach a forwardmost position, and the rear limit switch 39 is tripped when the ram assembly 23 reaches a rearwardmost position.

Referring to FIGS. 2-6, the tablet support mechanism 13 includes a rectangular housing 51 mounted on the front surface of the front frame wall 22. Within the housing 51 are horizontally slidably mounted right and left, horizontally opposed U-shaped members 52 and 53 respectively, each opening inwardly. The U-shaped members 52, 53 are slidably secured within the housing 51 by right and left mounting plates 55 and 56 which are secured to opposite sides of the housing 51. Adjustment knobs 57, 58 are mounted on respective outer ends of threaded shafts 61, 62, which shafts 61, 62 are threadedly coupled with threaded holes 63, 64 in central portions of the U-shaped members 52, 53. Right and left wires 67, 68 are strung in parallel between the leg portions of the U-shaped members 52, 53, respectively. The wires 67, 68 are preferably at least about one inch long, are preferably ⅛ inch or less in diameter, and most preferably 1/32 inch or less in diameter. The ends of wires 67, 68 pass through small holes (not shown) in the leg portions of the U-shaped members 52, 53 and are secured therein by set screws. The knobs 57, 58 can be operated to adjust the position of U-shaped members 52, 53 and hence adjust the horizontal spacing between the wires 67, 68. The wires 67, 68 comprise the support members for the tablet, and the spacing therebetween is adjustable in order to allow the wires to support tablets of varying sizes or shapes.

The U-shaped members 52, 53 are slidably mounted on a pair of parallel front and rear stepped portions 72 and 73 formed in the front and rear walls 74, 75 of the housing 51, respectively. The top wall 77 of housing 51 has an aperture therein which defines a window 78 through which the tablet dispenser moves to place a tablet on the wires 67, 68. The wires 67, 68 can be moved far apart as shown by dotted lines in FIG. 2.

Figure 3:
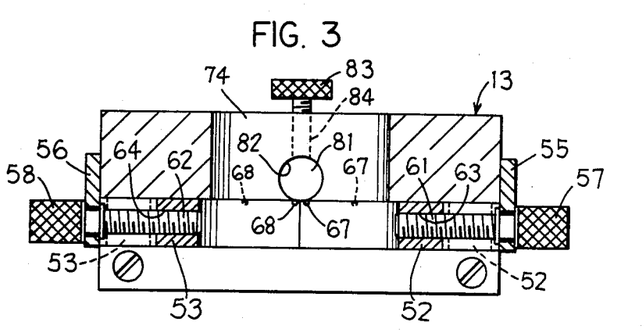
FIG. 3 is a cross-sectional view along line III—III in FIG. 2.

Referring to FIG. 3, an adjustable cylindrical anvil 81 is positioned in a circular through-hole 82 in the front wall 74. A set screw 83 threadedly coupled into a vertical threaded hole 84 in the wall 74 is used to secure the anvil 81 into a desired position. The anvil 81 is coaxially aligned with the ram 29. The anvil 81 and ram 29 are themselves positioned directly above the horizontal plane defined by support wires 67, 68 (see FIG. 4).

The tablet dispensing mechanism 11 is best shown in FIGS. 4–7. The tablet dispensing mechanism 11 includes a motor 87 having a rotatable crank (not shown) for vertically reciprocating a vertical plate 88 along a pair of vertical keyways defined by a C-shaped bracket 89. One end of the rotatable crank reciprocates along an elongated slot 90 in the plate 88. A cantilevered support arm 91 is secured at one end thereof to the vertical plate 88 for integral movement therewith. The support arm 91 is preferably made of hard plastic, such as Delrin (acetal resin). A limit switch 92 is positioned above the plate 88 so as to be tripped when the plate 88 moves to an uppermost position. A tablet dispenser 93 is slidably mounted in a first through-hole 90 extending vertically through said arm 91 at the end thereof remote from the plate 88.

Figure 7:
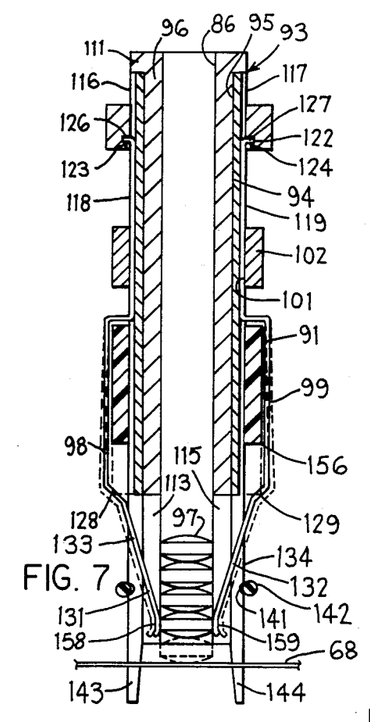
FIG. 7 is a cross-sectional view along line VI—VI in FIG. 6.

As shown in FIG. 7, the tablet dispenser 93 comprises a hollow cylinder 94 having a central bore 95 in which a tubular magazine 96 containing a stack of tablets 97 in a central bore 86 thereof is inserted. The magazine 96 has a flange 111 at the top end thereof, and has a radially extending roll pin 112 (FIG. 8) adapted to engage an internal groove (not shown) in the bore 95 of the cylinder 94, so that the magazine 96 can be axially inserted into the bore 95 and then rotated so that the roll pin 112 locks the magazine 96 into engagement with the cylinder 94 by means of a bayonet-type connection. Magazine 96 also has a pair of diametrically opposite, axially extending rectangular slots 113, 115 formed at the bottom thereof as shown in FIG. 7.

A pair of vertically elongated leaf springs 98, 99 are mounted on opposite sides of the outer periphery of cylinder 94. The cylinder 94 has an upper threaded portion 114 and a pair of parallel axial grooves 116, 117 formed in the outer periphery thereof diametrically opposite one another. Straight upper ends of upper Z-shaped portions 118, 119 of springs 98, 99, respectively, are positioned in the associated portions of grooves 116, 117, respectively. The upper portions 118, 119 are Z-shaped because the springs must extend around the outside of the arm 91, as shown in FIG. 7. A nut 121 is mounted on the threaded portion 114 of the cylinder 94. The nut 121 has an internal annular groove 122 and a pair of vertical grooves 123, 124 which extend downwardly. The upper portions 118, 119 of springs 98, 99 have radially outwardly turned ends 126, 127 which are in engagement with the annular groove 122. Due to this engagement, rotation of nut 121 causes vertical adjustment in the position of springs 98, 99.

The springs 98, 99 further define a pair of inwardly and downwardly extending contact portions 128, 129 which come into contact with the lower edge of the arm 91 when the arm 91 moves downwardly along the surface of the cylinder 94. A pair of lower portions 131, 132 of springs 98, 99 respectively function as tablet retaining arms. These tablet retaining arms 131, 132 resiliently engage the side surface of the lowermost tablet in the stack 97 at opposite sides thereof. The arms 131, 132 thereby retain the stack 97 within the central bore 86 of the magazine 96. The retaining arms 131, 132 extend inwardly relative to cylinder 94 through elongated axial slots 133, 134, respectively, in the cylinder 94. The slots 133, 134 are colinear with and represent continuations of the vertically elongated slots 116, 117, respectively. An annular groove 141 is formed in the outer periphery of the cylinder 94, which groove 141 intersects the axial slots 133, 134. An elastomeric O-ring 142 is held in resilient engagement with the annular groove 141 for maintaining the retaining arms 131, 132 within the bore 86. The slots 113, 115 of the magazine 96 are in alignment with the slots 133, 134 so that the retaining arms 131, 132 can extend radially inwardly through the cylinder 94 and magazine 96 to engage the lowermost tablet in the stack 97. The lower end of the cylinder 94 has two pairs of downwardly extending projections 143, 144 on opposite sides thereof, which projections cause an extension of the slots 133, 134. These projections 143, 144 are adapted to project below the level of the wires 67, 68 when the tablet dispenser 93 reaches its lowest position.

Figure 6:
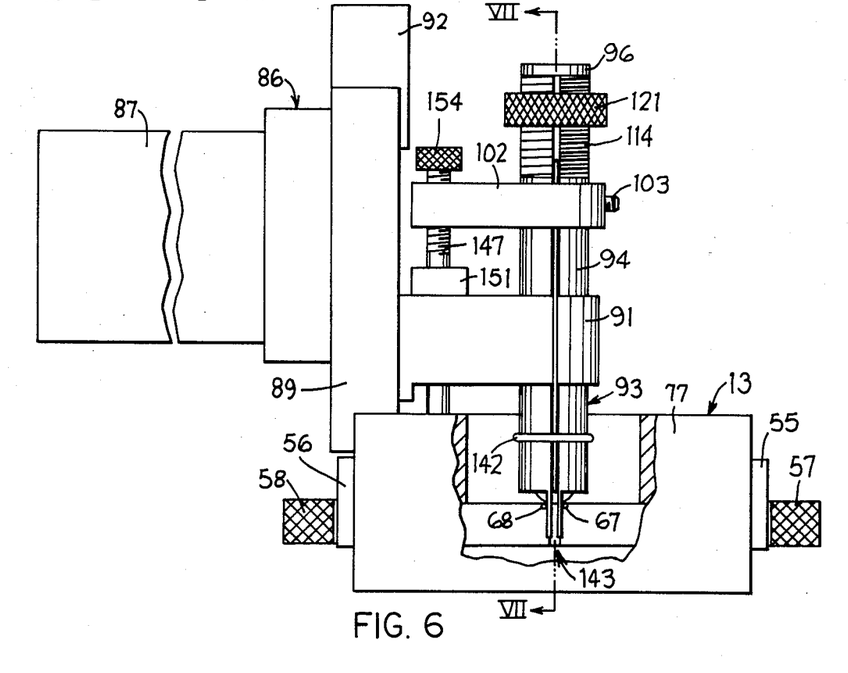
FIG. 6 is an end view like FIG. 4 except that the tablet dispenser is in its lowermost position.

The cylinder 94 is also mounted in a first, vertical, cylindrical through-hole 101 of a crosspiece 102. A set screw 103 extends through a threaded lateral hole 104 and is tightened to rigidly secure the crosspiece 102 to the cylinder 94. The crosspiece 102 has a second vertical, cylindrical, threaded through-hole 146 extending therethrough parallel to the first hole 101. A stop member or bar 147 which has threads on an upper end portion thereof is threadedly secured in the hole 146. The arm 91 similarly has a second vertical, cylindrical through-hole 148 formed therein which is coaxial with the hole 146. The arm 91 further has an upwardly extending cylindrical projection 151 which defines an upper end portion of the hole 148 and is adapted to come into engagement with the lower face of the crosspiece 102. The bar 147 is slidably mounted in the hole 148, extends below the arm 91, and has a lower end face 152 which engages the top wall 77 of the housing 51 when it reaches its lowermost position, as shown in FIG. 6. The crosspiece 102 rigidly connects the bar 147 to the cylinder 94, so that the cylinder 94, crosspiece 102 and bar 147 move as an integral unit. A knob 154 is formed at the upper end of the bar 147 to facilitate rotation of the bar 147 relative to the crosspiece 102 to adjust the position of stop face 152.

OPERATION

Figures 4, 8:
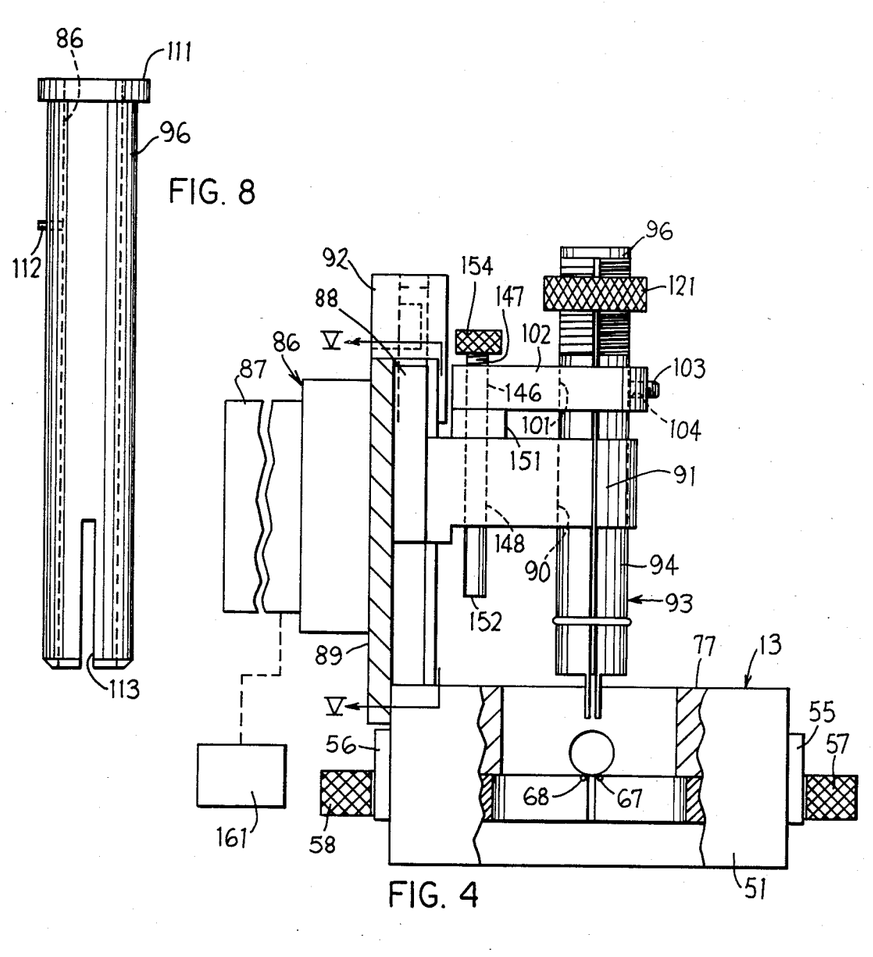
FIG. 4 is an end view, partly in section, showing the hardness tester in an uppermost position.
FIG. 8 is a front view of a tablet magazine.

The preferred embodiment of the hardness tester 11, as described above, operates as follows. A magazine 96 is selected which has a bore 86 of a diameter appropriate to the size of the tablets to be tested. The stack of tablets 97 is formed by loading tablets into the magazine 96, with the stack being held in the magazine by a removable elastic plug positioned in the lower end of the magazine. The magazine 96 is inserted into the cylinder 94 and secured therein by means of the bayonet connection. The elastic plug is then removed from the magazine, whereby the lowermost tablet is held by the retaining arms 131, 132 as in FIG. 7. At this time, the tablet dispenser 93 is at its uppermost position as shown in FIG. 4.

Figure 5:
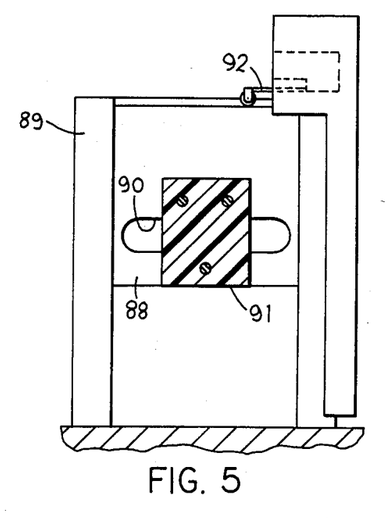
FIG. 5 is a cross-sectional view along line V—V in FIG. 4.

Using a control mechanism 161, the operator initiates a cycle of the motor 87. The motor 87 causes the plate 88 and arm 91 mounted thereon to move downwardly. The assembly of the tablet dispenser 93, crosspiece 102 and bar 147 moves downwardly in unison with the arm 91 due to the force of gravity. As this downward motion continues, the lower face 152 of bar 147 comes into engagement with the stop surface 77, preventing further downward movement of the bar 147, crosspiece 102 and tablet dispenser 93. The arm 91, however, continues to move downwardly. This downward motion of arm 91 relative to the tablet dispenser 93 causes the arm 91 to reach the dotted position shown in FIG. 7. At this time, the position of the apparatus is substantially as shown in FIG. 6. The lowermost tablet in the stack 97 is positioned approximately one tablet width above the wires 67, 68, and the projections 143, 144 extend below and between the wires 67, 68. If fragments of a previously crushed tablet remain on the wires 67, 68, the downward motion of the projections 143, 144 dislodges any fragments which remain on the wires 67, 68, and such fragments fall into the receptacle 14. Generally, the fragments of a crushed tablet fall into the receptacle 14 of their own accord without having to be pushed by the projections 143, 144. In practice, is it found that the projections 143 are the only ones which actually encounter tablet fragments, since the direction of travel of the ram along the top of the wires 67, 68 is from right to left as shown in FIG. 5, effectively pushing any remaining fragments toward the projections 143 and away from the projections 144. The projections 144 may accordingly be omitted.

When the arm 91 reaches the dotted position shown in FIG. 7, and the tablet dispenser 93 has already reached its lowermost position as shown in FIG. 6, the lower outside corner 156 of arm 91 engages the inwardly extending contact portions 128, 129 of springs 98, 99. The contact portions 128, 129 slope both downwardly and radially inwardly so that contact between corner 156 and portions 128, 129 effectively urges the tablet retaining arms 131, 132 apart. Tablet engaging portions 158, 159 which comprise substantially vertically extending tips of the retaining arms 131, 132 at the lowermost ends thereof, respectively, become disengaged from the lowermost tablet by the outward motion of the retaining arms, and the entire stack 97 drops by one tablet thickness until the lowermost tablet rests on the wires 67, 68, assuming the position shown by dotted lines in FIG. 7.

At this point, the cycle of the motor 87 begins to move the plate 88 and arm 91 upwardly, bringing the arm 91 out of engagement with the shoulder portions 128, 129. The retaining arms 131, 132 resiliently return inwardly and accordingly move the tablet engaging portions 158, 159 inwardly into engagement with the side surface of the next tablet above the former lowermost tablet. The arm 91 continues to move upwardly relative to cylinder 94 until the projection 151 engages the lower face of the crosspiece 102. After this contact is made, the bar 147, crosspiece 102 and dispenser 93 move upwardly in unison with the arm 91. This movement continues until the plate 88 trips the limit switch 92, which turns off the motor 87 and initiates the cycle of the motor 16 in the ram mechanism 12. When the limit switch 92 is tripped, the tablet dispenser 93 has been moved upwardly out of the path of the ram 29.

Actuation of the motor 16 causes the rotation of a primary drive shaft (not shown) to be transmitted to the threaded drive shaft 26 via the driving gear 18. The threaded drive shaft 26 is rotated in a direction such that the ram assembly 23 moves forwardly (leftwardly in FIG. 2). The ram 29 moves through the hole 30 out over the wires 67, 68. The ram 29 continues to move above and parallel to the lengthwise direction of the wires 67, 68, directly toward the tablet resting thereon and the anvil 81. Eventually the tablet is clamped between the ram 29 and the anvil 81, and provides resistance to the continued movement of the ram 29. This resistance is measured by the strain gauge transducer 28, which is electrically connected to a strain gauge indicator such as an oscilloscope or a digital readout device which directly measures the force exerted on the tablet. The force reading reaches a maximum at the moment the tablet fractures, and this reading is recorded. The ram assembly then continues to move forwardly until the cam 37 trips the front limit switch 38. Should the front limit switch 38 fail, the ram assembly 23 continues to move forward until the auxiliary front limit switch 47 is tripped by the cam 36.

When either of the limit switches 38 or 47 is tripped, the cycle of the motor 16 is reversed, and the threaded drive shaft 26 is driven in the opposite direction so that the ram assembly 23 moves rearwardly and the ram 29 moves away from the anvil 81. The ram assembly 23, moving together with the linear bushings 32, 33, continues to move rearwardly until the cam 37 trips the rear limit switch 39. If the limit switch 39 fails, the ram assembly continues to move rearwardly until the auxiliary rear limit switch 48 is tripped. Tripping of either rear limit switch 39 or 48 turns off the motor 16, and the ram assembly 23 remains at the position substantially as shown in FIG. 2.

At this time, the apparatus can be set to repeat another cycle, beginning with the actuation of the motor 87 as described above, assuming that tablets remain in the magazine 96. The operation can be repeated cyclically until all of the tablets in the stack 97 have been dispensed. In the alternative, each cycle of the apparatus can be initiated manually by the operator. The apparatus according to the present invention can also include means for automatically ceasing operation once all of the tablets have been dispensed from the magazine 96.

By the foregoing procedure, a series of identical tablets can be tested rapidly without need for a separate manual or automatic cleaning operation between each test. Such a cleaning operation is not needed because the crushed fragments of the tested tablet fall into the receptacle positioned below the wires due to the force of gravity. If by chance any fragment of the tablet should remain balanced on the wires, the projections 143, 144 are effective to dislodge such fragments and cause them to fall into the box. An important preferred feature of the present invention is that the direction of travel of the ram be horizontal, and the direction of travel of the tablet dispensing mechanism be vertical, as illustrated in the above-described embodiment. This arrangement effectively utilizes the force of gravity both for removing the tablet fragments from the crushing zone and for executing the movements of the tablet dispenser 93.

The precise configuration of the springs 98, 99 is not essential so long as a pair of resilient retaining arms are used to engage the lowermost tablet of the stack of tablets. The magazine 96 can have additional lengthwise rectangular openings in the sides thereof designed to accommodate tablets of noncircular shape, such as elliptical tablets.

The cycle of the hardness tester 10 according to the invention is as follows. A start switch 161 is used by an operator to actuate the motor 87. The limit switch 92 turns off the motor 87 after the completion of a cycle and at substantially the same time activates the motor 16 to drive the ram assembly 23 forwardly. When the tablet is fractured, the strain gauge transducer 28 relays the force measurement to a conventional digital indicator 162, where it may be read by the operator. Shortly thereafter, one of the front limit switches 38 or 47 causes the motor 16 to reverse the direction of rotation of the drive shaft 26, moving the ram assembly 23 rearwardly until either one of the rear limit switches 39 or 48 deactivates the motor 16. The foregoing steps define a complete measurement cycle for one tablet using the aforesaid embodiment of the invention. Another cycle may then be manually initiated, or the apparatus may be set to run continuously.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exqlusive property or privilege is claimed are defined as follows:

1. In an apparatus for measuring tablet hardness, including ram and anvil means for fracturing a tablet therebetween; means for supporting a tablet in position for fracturing between said ram and anvil means, means for measuring the force exerted by said ram which is sufficient to fracture said tablet, and means for indicating the force measured by said measuring means, the improvement which comprises:

said supporting means comprises a plurality of horizontal, spaced-apart, elongated support members for supporting the underside of a tablet, said members having a diameter small enough so that pieces of said tablet, after said tablet has been fractured by said ram and anvil means, can fall past and below said support members.

2. An apparatus as claimed in claim 1, wherein said support members comprise a pair of parallel wires, and said supporting means including a housing, a pair of U-shaped members mounted on said housing, said U-shaped members opening horizontally inwardly in opposite directions, each of said U-shaped members having one of said wires tightly strung between opposite ends of said U-shaped member, and the separation between said wires being adjustable by horizontal movement of said U-shaped members on said housing.

3. An apparatus as claimed in claim 1, further comprising means for dispensing a lowermost tablet of a vertical stack of tablets onto said support members.

4. An apparatus as claimed in claim 3, wherein said dispensing means moves vertically to deposit a tablet on said supporting means, and said ram moves horizontally to crush the thus-placed tablet.

5. An apparatus as claimed in claim 4, wherein said dispensing means comprises a cylindrical tablet dispenser which contains said stack of tablets therein, means for reciprocating said cylindrical tablet dispenser upwardly and downwardly between an uppermost position at which said dispenser is clear of the path of movement of said ram and a lowermost position at which said dispenser is in position to deliver the lowermost tablet of said stack of tablets onto said support members, means for releasing said lowermost tablet from said dispenser so that said lowermost tablet rests on said support members, and means for retaining the remainder of said stack of tablets within said cylindrical dispenser as said dispenser moves upwardly after having deposited the lowermost tablet onto said support members.

6. An apparatus as claimed in claim 4, wherein said ram and anvil means comprises a reversible motor, a threaded drive shaft rotatable by said motor, a cylindrical sleeve threadedly mounted on said drive shaft at the rear end of said sleeve, a strain gauge transducer connected to the front end of said sleeve at the rear end of said transducer, a ram member connected to the front end of said transducer at the rear end of said ram member, and means for controlling movement of the assembly of said sleeve, transducer and ram member between a forwardmost position and a rearwardmost position, said ram member moving forwardly along a path parallel to and above the lengthwise direction of said support members until said ram member contacts the tablet to be tested, then clamps said tablet between said ram member and said anvil, then fractures said tablet, said strain gauge transducer functioning to measure the force required to fracture said tablet, after which said ram member moves rearwardly to said rearwardmost position.

7. An apparatus as claimed in claim 6, wherein said ram and anvil means further comprises a frame, a pair of horizontal parallel guide shafts mounted on opposite sides of said threaded drive shaft, said sleeve, said transducer and said cylindrical ram, a pair of linear bushings slidably mounted on said guide shafts, and a bracket connecting said ram assembly to said linear bushings for integral movement therewith.

8. An apparatus as claimed in claim 4, wherein said tablet dispensing means comprises a motor, a plate adapted to be reversibly vertically moved by said motor, an arm fixedly mounted on said plate at one end of said arm, said arm having a first, vertically extending hole therein, a tablet dispenser slidably mounted in said first hole, which tablet dispenser places a tablet on said support members when said arm and said plate are moved to a lowermost position by actuation of said motor, and means for actuating said ram when said tablet dispenser has moved upwardly out of the path of movement of said ram.

9. An apparatus as claimed in claim 8, wherein said arm has a second, vertically extending hole therein located between said first hole and said one end of said arm mounted to said plate, said tablet dispenser comprises a cylinder having a central, vertically extending bore therein, a pair of leaf springs having lower end portions which resiliently engage opposite side edges respectively of a lowermost tablet in a vertical tablet stack located within said bore of said cylinder, thereby retaining said stack in said bore of said cylinder, said springs being mounted on said cylinder, said cylinder being slidably movable within said first hole of said arm, a vertical elongated stop member slidably movable within said second hole in said arm, means for stopping said stop member at a lowermost position as said stop member slides within said second hole in said arm, means for rigidly connecting said stop member and said cylinder for integral movement with each other so that when said arm is moved vertically downwardly by actuation of said motor, so that said cylinder moves downwardly with said arm until said stop member engages said stopping means, then said arm continues to move downwardly relative to said cylinder and deforms said springs at contact portions thereof so that said lower portions of said springs release said lowermost tablet and said lowermost tablet falls into position on said support members, then said motor moves said arm upwardly so that said arm no longer deforms said springs and said lower portions of said springs engage opposite side edges of the tablet adjacent said lowermost tablet, whereafter said stack of tablets is then lifted together with said cylinder leaving only said lowermost tablet on said support members, and said arm then moves upwardly into contact with said rigid connection means so that said cylinder moves upwardly together with said arm to an uppermost position at which said tablet dispenser is positioned above the path of movement of said arm.

10. An apparatus as claimed in claim 9, further comprising a limit control switch positioned to be tripped when said cylinder reaches said uppermost position, which limit control switch functions to stop said motor and initiate reciprocal movement of said ram for fracturing the tablet supported on said support members.

11. An apparatus as claimed in claim 9, further comprising a removable magazine having a central bore therein, said magazine being positioned inside said cylinder coaxially therewith, said central bore of said magazine being shaped to maintain said tablets in a vertical stack.

12. An apparatus as claimed in claim 1, wherein said measuring means comprises a strain gauge transducer connected to said ram for measuring the force exerted by said ram on said tablet, and said indicating means comprises an electronic digital force indicator.

13. In an apparatus for measuring tablet hardness, including ram and anvil means for fracturing a tablet therebetween, means for supporting a tablet in position for fracturing between said ram and anvil means, means for measuring the force exerted by said ram which is sufficient to fracture said tablet, and means for indicating the force measured by said measuring means, the improvement which comprises:

means for supporting a vertical stack of tablets and for dispensing a lowermost tablet of the stack onto said support means, said dispensing means comprising a tablet dispenser which contains said stack of tablets therein, means for reciprocating said tablet dispenser upwardly and downwardly between an uppermost position at which said dispenser is clear of the path of movement of said ram and a lowermost position at which said dispenser is in position to deliver the lowermost tablet onto said support means, a plurality of resilient retaining arms mounted on said tablet dispenser, said arms engaging the lowermost tablet in said stack to thereby retain said stack within said dispenser, means for deforming said resilient arms and thereby release said lowermost tablet from said stack so that said lowermost tablet rests on said support means, and means for retaining the remainder of said stack of tablets within said dispenser as said dispenser moves upwardly after having deposited said lowermost tablet onto said support means by bringing said arms into resilient engagement with the next tablet above said lowermost table in said stack.

14. An apparatus as claimed in claim 13, further comprising a tablet magazine having a bore therein which holds said stack of tablets, said magazine being removably coupled to said tablet dispenser.

15. An apparatus as claimed in claim 13, further comprising an actuator slidably mounted on the outer periphery of said tablet dispenser, said actuator engaging said retaining arms to deform said arms and cause said arms to release said lowermost tablet, and said resilient arms comprise a pair of leaf springs mounted on opposite sides of said tablet dispenser and extending in the lengthwise direction thereof to engage said lowermost tablet on opposite sides of said lowermost tablet.

16. An apparatus as claimed in claim 13, wherein said support means comprises a pair of elongated, spaced-apart, parallel wires, and said dispensing means places said lowermost tablet so that said tablet rests on said wires.

17. In an apparatus for measuring hardness, including ram and anvil means for fracturing an object therebetween; means for supporting the object in position for fracturing between said ram and anvil means, means for measuring the force exerted by said ram which is sufficient to fracture the object, and means for indicating the force measured by said measuring means, comprising the improvement wherein:

said supporting means comprises a plurality of horizontal, spaced-apart, elongated support members for supporting the underside of the object, said members having a diameter small enough so that pieces of the object, after the object has been fractured by said ram and anvil means, can fall past and below said support members.

18. An apparatus as claimed in claim 17, wherein said support members comprise a pair of parallel wires, and said supporting means including a housing, a pair of U-shaped members mounted on said housing, said U-shaped members opening horizontally inwardly in opposite directions, each of said U-shaped members having one of said wires tightly strung between opposite ends of said U-shaped member, and the separation between said wires being adjustable by horizontal movement of said U-shaped members on said housing.

19. An apparatus as claimed in claim 17, wherein said ram and anvil means comprises a reversible motor, a threaded drive shaft rotatable by said motor, a cylindrical sleeve threadedly mounted on said drive shaft at the rear end of said sleeve, a strain gauge transducer connected to the front end of said sleeve at the rear end of said transducer, a ram member connected to the front end of said transducer at the rear end of said ram member, and means for controlling movement of the assembly of said sleeve, transducer and ram member between a forwardmost position and a rearwardmost position, said ram member moving forwardly along a path parallel to and above the lengthwise direction of said support members until said ram member contacts the object to be tested, then clamps said object between said ram member and said anvil, then fractures said object, said strain gauge transducer functioning to measure the force required to fracture said object, after which said ram member moves rearwardly to said rearwardmost position.

20. An apparatus as claimed in claim 19, wherein said ram and anvil means further comprises a frame, a pair of horizontal parallel guide shafts mounted on opposite sides of said threaded drive shaft, said sleeve, said transducer and said cylindrical ram, a pair of linear bushings slidably mounted on said guide shafts, and a bracket connecting said ram assembly to said linear bushings for integral movement therewith.

21. An apparatus as claimed in claim 17, wherein said support means comprises a pair of elongated, spaced-apart, parallel wires.

22. An apparatus as claimed in claim 21, wherein said measuring means comprises a strain gauge transducer connected to said ram for measuring the force exerted by said ram on said object, and said indicating means comprises an electronic digital force indicator.

* * * * *

UNITED STATES PATENT AND TRADEMARK OFFICE
CERTIFICATE OF CORRECTION

PATENT NO. : 4 542 646
DATED : September 24, 1985
INVENTOR(S) : Daniel J. SMITH et al It is certified that error appears in the above-identified patent and that said Letters Patent is hereby corrected as shown below:

Column 2, line 27; change "line VI-VI" to ---line VII-VII---.

Column 7, line 43; change "and the anvil" to ---and toward the anvil---.

Signed and Sealed this

Eleventh Day of February 1986

[SEAL]

Attest:

DONALD J. QUIGG

Attesting Officer

Commissioner of Patents and Trademarks